US010617780B2

(12) United States Patent
Dombrowski et al.

(10) Patent No.: US 10,617,780 B2
(45) Date of Patent: Apr. 14, 2020

(54) DISINFECTANT CAPS

(71) Applicant: 3M INNOVATIVE PROPERTIES COMPANY, Saint Paul, MN (US)

(72) Inventors: Alan R. Dombrowski, Woodbury, MN (US); Timothy C. McFarland, Minneapolis, MN (US); John C. Detloff, San Diego, CA (US)

(73) Assignee: 3M Innovative Properties Company, Saint Paul, MN (US)

( * ) Notice: Subject to any disclaimer, the term of this patent is extended or adjusted under 35 U.S.C. 154(b) by 124 days.

(21) Appl. No.: 15/623,430

(22) Filed: Jun. 15, 2017

(65) Prior Publication Data

US 2018/0361003 A1    Dec. 20, 2018

(51) Int. Cl.
| A61L 2/26 | (2006.01) |
| A61M 39/16 | (2006.01) |
| A61M 39/20 | (2006.01) |
| A61L 2/18 | (2006.01) |
| B29C 45/72 | (2006.01) |
| B29C 45/40 | (2006.01) |
| B29L 1/00 | (2006.01) |
| A61M 5/31 | (2006.01) |
| B22F 3/22 | (2006.01) |

(52) U.S. Cl.
CPC ...... *A61L 2/26* (2013.01); *A61L 2/18* (2013.01); *A61M 39/162* (2013.01); *A61M 39/20* (2013.01); *B29C 45/40* (2013.01); *B29C 45/7207* (2013.01); *A61L 2/186* (2013.01); *A61L 2202/24* (2013.01); *A61M 2005/312* (2013.01); *A61M 2207/00* (2013.01); *B22F 3/225* (2013.01); *B29L 2001/00* (2013.01)

(58) Field of Classification Search
CPC ... A61L 2/26; A61L 2/186; A61L 2/18; A61L 2202/24; A61M 39/20; A61M 39/162; A61M 2207/00; B29C 45/40; B29C 45/7207; B22F 3/225; B29L 2001/00
See application file for complete search history.

(56) References Cited

U.S. PATENT DOCUMENTS 3,737,277 A * 6/1973 Uhlig .................... B29C 33/485
                                                        249/59
4,084,716 A * 4/1978 Bogert ................. B65D 50/043
                                                        215/217
(Continued)

FOREIGN PATENT DOCUMENTS

WO    WO 2018/106508    6/2018

OTHER PUBLICATIONS

Section View of Version B of 3M Cap for Needless Connector, Infusion Nurses Society Annual Convention and Industrial Exhibition, Ft. Lauderdale, FL, May 14-19, 2016.

*Primary Examiner* — Regina M Yoo
(74) *Attorney, Agent, or Firm* — 3M Innovative Properties Company; Trisha D. Adamson

(57) ABSTRACT

A cleaning device for LADs, and other such threaded devices, comprising a cap and a cleaning agent. The cap comprises a casing having an opening to an interior cavity. A threaded coupling mechanism is located on the inner surface of the casing proximate the opening. The coupling mechanism has retention features that provide localized pressure points on the threads of the LAD to accommodate thread variance and reduce the chance of premature disengagement.

20 Claims, 4 Drawing Sheets

(56) References Cited

U.S. PATENT DOCUMENTS

| | | | | |
|---|---|---|---|---|
| 4,778,447 | A * | 10/1988 | Velde | A61M 39/10 604/29 |
| 5,169,033 | A * | 12/1992 | Shay | B05B 11/3045 215/216 |
| 5,292,020 | A * | 3/1994 | Narin | B65D 41/0471 215/330 |
| 5,584,420 | A * | 12/1996 | Awada | G01F 11/263 222/153.09 |
| 7,007,817 | B2 * | 3/2006 | Jochem | B29C 37/0085 215/305 |
| 7,780,794 | B2 | 8/2010 | Rogers | |
| 8,172,825 | B2 * | 5/2012 | Solomon | A61M 39/162 604/256 |
| 8,491,546 | B2 | 7/2013 | Hoang | |
| 9,907,617 | B2 * | 3/2018 | Rogers | A61L 2/186 |
| 2011/0265825 | A1 | 11/2011 | Rogers | |
| 2012/0039764 | A1 * | 2/2012 | Solomon | A61M 25/0097 422/292 |
| 2012/0216359 | A1 | 8/2012 | Rogers | |
| 2015/0034673 | A1 * | 2/2015 | Hopkins | B65D 47/243 222/129 |
| 2017/0203087 | A1 * | 7/2017 | Ryan | A61M 39/20 |
| 2017/0203092 | A1 * | 7/2017 | Ryan | A61M 39/20 |

\* cited by examiner

DISINFECTANT CAPS

FIELD OF INVENTION

The present invention relates to disinfectant caps for threaded devices, such as needleless connectors, and methods of making such.

BACKGROUND

Needleless connectors or luer activated devices (LADs) are used in the medical profession for fluid transfer processes. LADs may be disconnected and reconnected to fluid lines multiple times during use and, therefore, subject to contamination from pathogens, including bacteria and viruses, in-between connections. The traditional approach to reducing contamination has been to swab the end of the luer with an alcohol pad and let the alcohol dry (e.g., 20-30 seconds) prior to making any connection with the LAD (i.e. scrub-the-hub). More recently, efforts have focused on replacing the scrub-the-hub technique with disinfectant caps containing a cleaning agent. The disinfectant caps can remove potential contaminants and protect the end of the LAD from further contamination between uses. Examples of such disinfectant caps can be found in U.S. Pat. No. 7,780,794.

SUMMARY

The present disclosure describes a cleaning device for LADs, and other such threaded devices, comprising a cap and a cleaning agent. The cap comprises a casing having an opening to an interior cavity. A threaded coupling mechanism is located on the inner surface of the casing proximate the opening. The coupling mechanism has retention features that provide localized pressure points on the threads of the LAD to accommodate thread variance and reduce the chance a cap will prematurely disengage from the LAD.

In one embodiment, the present disclosure provides a cap comprising a casing having an opening to an interior cavity, the casing having an inner surface and an outer surface, and a coupling mechanism on the inner surface of the casing proximate the opening. The coupling mechanism comprises a thread that starts proximate the opening and spirals into the interior cavity. The coupling mechanism further comprises a first lug and a second lug, wherein the first and second lugs do not intersect the thread. The first lug is closer to the opening of the casing than the second lug, and the volume of the second lug is greater than the volume of the first lug.

In another embodiment, the present disclosure provides a cleaning device comprising a cap and a cleaning agent. The cap comprises a casing having an opening to an interior cavity, the casing having an inner surface and an outer surface, and a coupling mechanism on the inner surface of the casing proximate the opening. The coupling mechanism comprises a thread that starts proximate the opening and spirals into the interior cavity. The coupling mechanism further comprises a first lug and a second lug, wherein the first and second lugs do not intersect the thread. The first lug is closer to the opening of the casing than the second lug, and the volume of the second lug is greater than the volume of the first lug. The cleaning agent is in the interior cavity of the casing.

The above summary of the present disclosure is not intended to describe each disclosed embodiment or every implementation of the present disclosure. The description that follows more particularly exemplifies illustrative embodiments.

Figure 1:
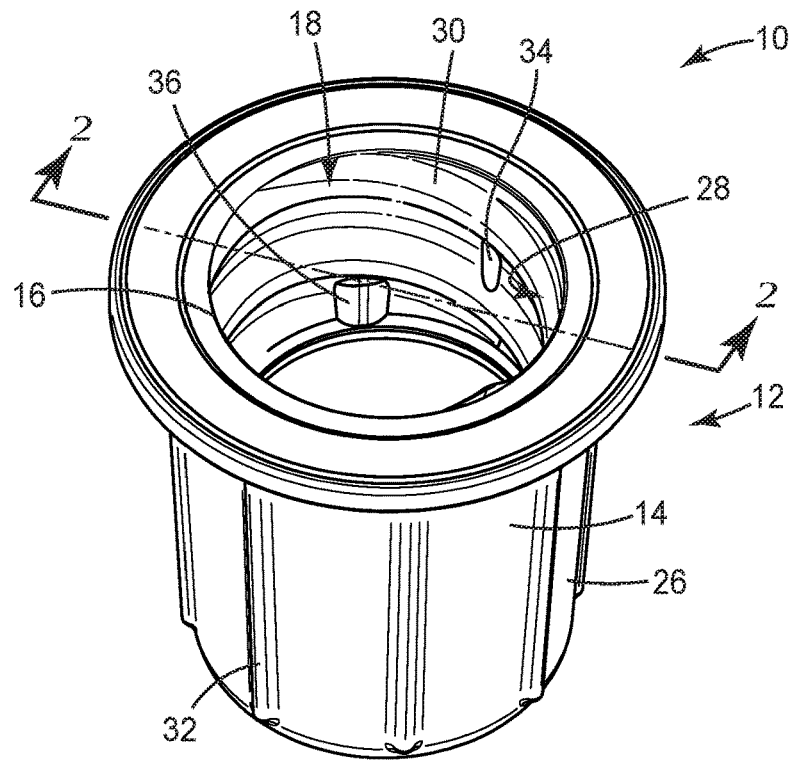
FIG. 1 is a top perspective view of an exemplary cleaning device of the present application.

Unless otherwise indicated, all figures and drawings in this document are not to scale and are chosen for the purpose of illustrating different embodiments of the invention. In particular, the dimensions of the various components are depicted in illustrative terms only, and no relationship between the dimensions of the various components should be inferred from the drawings, unless so indicated.

DETAILED DESCRIPTION

Despite the presence of disinfectant caps currently in the market space, there is a need to address the small, but noticeable, variance in LAD threads across manufacturers. This variance can lead to premature disengagement of a disinfectant cap from certain LADs during use. Although LADs are manufactured to an ISO standard (594-2), slight variations in threading (e.g., number of revolutions, shape, and pitch) can prevent the cap from securing properly to the LAD and cause accidental disengagement through, for example, repeated bumping or jostling of the LAD or the cap threaded thereon. The caps described herein comprise retention features that adapt to LAD thread variance, thus reducing the chance a cap will prematurely disengage from the LAD.

Before any embodiments of the present disclosure are explained in detail, it is to be understood that the phraseology and terminology used herein is for the purpose of description and should not be regarded as limiting. As used herein, the terms "including," "comprising," or "having" and variations thereof encompass the items listed thereafter and equivalents thereof, as well as additional items. All numerical ranges are inclusive of their endpoints and non-integral values between the endpoints unless otherwise stated.

Generally, the cleaning devices of the present application comprise a cap and a cleaning agent contained therein. The cap is configured to securely fit over an exposed portion of an externally threaded device, such as the luer threading of a LAD, thus bringing the exposed portion in contact with a cleaning agent. The cleaning agent can generally be any substance or material that cleans a device (e.g., LAD) of bacterial and/or viral microorganisms and includes antibacterial and antifungal agents, antiseptic or antimicrobial agents, wide spectrum disinfectants, and/or parasiticides, as well as combinations of such. Exemplary cleaning agents include alcohols (e.g., isopropyl alcohol and ethanol), alcohols at various concentrations (e.g., 70%/30% v/v isopropyl alcohol/water), chlorhexidine (e.g., chlorhexidine gluconate, chlorhexidine acetate), povidone-iodine, hydrogen peroxide, soap, hydrochloric acid, chloroxylenol (PMCX), polyhexamethylene biguanide (PHMB), octenidene, benzalkonium chloride, and combinations thereof. The cap can remain on the LAD until ready to use, thus protecting the LAD from further contamination. Although the cleaning devices of the present application will be exemplified for use with LADs, it should be understood that the cleaning devices can be readily adapted and broadly applied to any externally threaded device.

Figure 2:
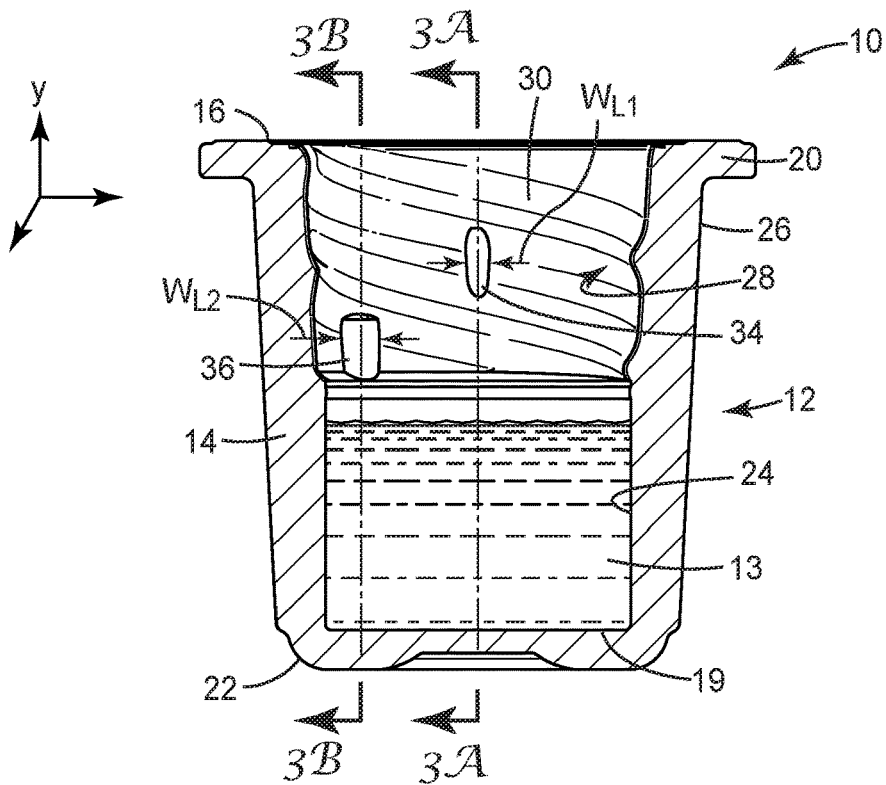
FIG. 2 is a cross-sectional view of the cleaning device shown in FIG. 1 taken along line 2-2 in FIG. 1.

FIGS. 1 and 2 illustrate a first exemplary cleaning device 10 of the present application comprising a cap 12 and a cleaning agent 13. The cap 12 comprises a casing 14 having an opening 16 to an interior cavity 18. The casing 14 has a top 20, a bottom 22, an inner surface 24 and an outer surface 26. The outer surface 26 of the casing 14 optionally includes gripping features 32 that are spaced around the outer surface 26 of the casing 14 to facilitate manual manipulation of the cap 12 during use.

A removable protective seal (not shown) can be applied across the opening 16 of the casing 14 to prevent loss of cleaning agent 13 and maintain sterility of the interior cavity 18 of the cap 12 prior to use. The seal (e.g., a foil seal) can be secured to the top 20 of the casing 14 by, for example, glue, solvent or thermal bonding. In some embodiments, the seal may be configured for multiple caps, such as a strip of foil where individual caps can be peeled from the strip as needed. These strips of caps can be made conveniently accessible by hanging them, for example, from intravenous (IV) poles or IV sets in patient rooms and on medication carts.

Although the casing 14 in FIG. 1 has a relatively cylindrical shape, the casing shape is not particularly limited as long as the coupling mechanism (described below) is configured to engage with the LAD. In some embodiments, at least a portion of the casing has a frustoconical shape. In other embodiments, at least a portion of the casing has a bulbous configuration (e.g., rounded bottom). The casing may be a unitary structure, as shown in FIG. 1, or made from two or more components joined together. For example, the cap in FIG. 1 could be made by joining a cylindrical-shaped wall and a circular, flat bottom together with glue, welding, solvent, threads or other attachment mechanism.

The casing 14 can be made from a variety of materials, including plastic, glass and metal. In some embodiments, the casing is formed from a resilient material, such as a resilient thermoplastic material. The resilient material provides for flexing or expansion of the casing in response to forces generated by the LAD when threading the cap onto the LAD device. A resilient material, as used herein, refers to a material that when used in the intended application deflects without permanent deformation in response to an applied force and returns to its original position when that applied force is removed. The resiliency of the casing is influenced by the type of material used to form the casing and the thickness of the casing. The resiliency can be sufficient to permit slight expansion of the casing for device threads with larger diameters while still exerting sufficient pressure on the device to create friction between the coupling mechanism and the device.

Preferably, the casing is made from a thermoplastic material. As used herein, the term "thermoplastic material" means a plastic material that has a softening or melting point, and is substantially free of a three-dimensional cross-linked network resulting from the formation of covalent bonds between chemically reactive groups, e.g., active hydrogen groups and free isocyanate groups. Examples of thermoplastic materials include, but are not limited to, thermoplastic polyalkylenes, thermoplastic polyurea, thermoplastic polyimide, thermoplastic polyamide, thermoplastic polyamideimide, thermoplastic polyester, thermoplastic polycarbonate, thermoplastic polysulfone, thermoplastic polyketone, thermoplastic polyethylene, thermoplastic polypropylene, thermoplastic polybutylene terephthalate, thermoplastic polyvinylchloride, thermoplastic acrylonitrile-butadiene-styrene, thermoplastic polyurethane and mixtures of thermoplastic compositions containing one or more thereof. In some embodiments, the casing is made from high-density polyethylene (HDPE).

Figure 3A:
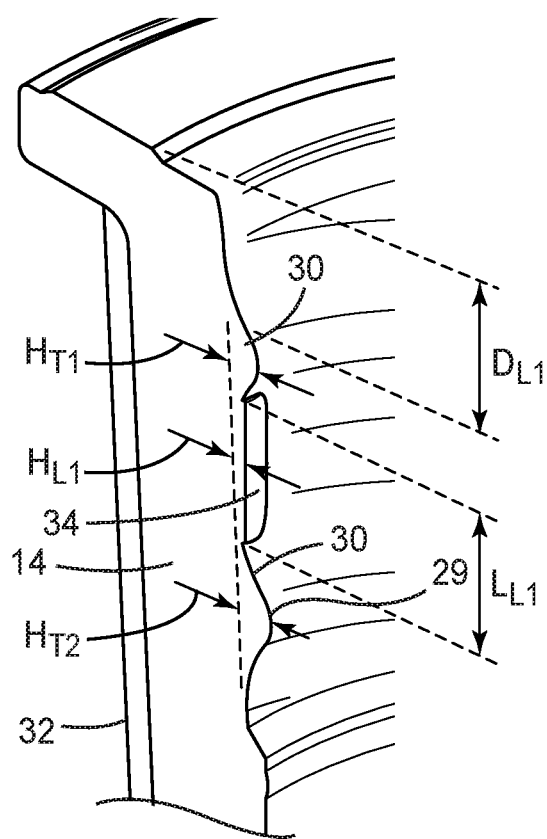
FIG. 3A is a cross-sectional view of a portion of the cleaning device shown in FIGS. 1 and 2 taken along line 3A-3A in FIG. 2.
Figure 3B:
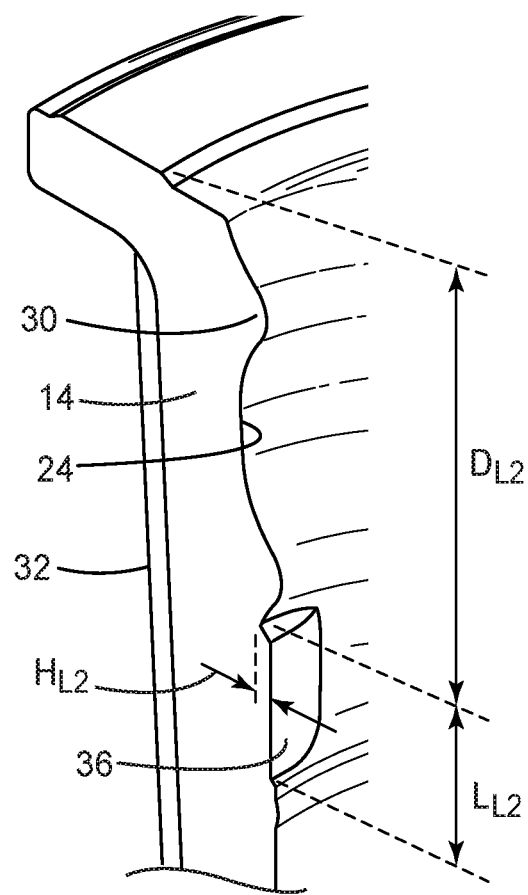
FIG. 3B is a different cross-sectional view of a portion of the cleaning device shown in FIGS. 1 and 2 taken along line 3B-3B in FIG. 2.

As further illustrated in FIGS. 1-3, a coupling mechanism 28 is located on the inner surface 24 of the casing 14 proximate the opening 16. The coupling mechanism 28 is configured to engage with an externally threaded device, such as a LAD. The coupling mechanism 28 may be unitary with the casing 14, as illustrated in FIGS. 1 and 2 or a separate component that is joined to the inner surface of the casing by, for example, glue or welding. The coupling mechanism may be made from the same material as the casing, or a different material. In some embodiments, the casing and coupling mechanism are made from HDPE.

The coupling mechanism 28 comprises a thread 30 that originates proximate (i.e. at or near) the opening 16 and spirals downward along the inner surface 24 of the casing 14 to a predetermined depth into the interior cavity 18. In some embodiments, the thread 30 can extend past the midway point of the interior cavity 18 but terminate prior to reaching the bottom 19 of the interior cavity 18. For example, the upper 60% of the inner surface 24 of the casing 14 can include the thread 30, while the lower 40% of the inner surface 24 of the casing 14 can be devoid of the thread 30. Alternatively, the upper 40% of the inner surface 24 of the casing 14 can include the thread 30, while the lower 60% of the inner surface 24 of the casing 14 can be devoid of thread 30. It is understood that the penetration depth of the thread 30 into the interior cavity 18 can vary depending on the particular design of the cap 12.

The configuration of the thread 30 can also vary. For example, the thread may comprise a single thread or dual threads that do not intersect (e.g., a double start, right hand thread). The thread can be made from continuous threads, discontinuous threads, or combinations thereof.

In some embodiments, as illustrated in FIG. 3, the thread 30 has uniform height $H_T$ throughout (i.e. $H_{T1}=H_{T2}$). As used herein, the thread height, $H_T$, refers to the distance between the inner surface 24 of the casing 14 and the outer surface of the thread 30. For rounded threads, as illustrated in FIG. 3, the thread height is typically measured from the inner surface 24 of the casing 14 to the highest point (i.e., crest) 29 of the thread. In other embodiments, the thread height varies continuously or discontinuously throughout the coupling mechanism. For example, the height of the thread can gradually or incrementally increase as a function of increasing depth from the opening 16 of the casing 14 (i.e. $H_{T1}<H_{T2}$). This increase in thread height advantageously allows the cap to be used across a wide range of thread variance on different LADs. The shape of the thread (e.g., rounded or angular) may also vary and will often depend upon the method of manufacture.

Ideally, the thread of the coupling mechanism has a complimentary structure to the threads of the LAD and, once fully engaged, resists premature disengagement. However, the caps are typically made from a rigid or semi-rigid material and resistance to disengagement will vary within the thread tolerances observed for LADs. In an effort to provide a cleaning device that accommodates the range of thread tolerances, the caps of the present application have added retention features, in the form of lugs, to the coupling mechanism to minimize or reduce premature disengagement.

As illustrated in FIGS. 1-3, the coupling mechanism 28 includes at least two lugs, one positioned close to the opening (e.g., first lug 34) and one further into the interior cavity (e.g., second lug 36). Additional lugs may optionally be added. The lugs are made of a material that is softer (i.e., less hard) than the material that makes up the thread of the LAD. As the cap 12 is threaded onto the LAD, the thread of the LAD passes through one or more lugs of the cap, causing the lugs to plastically deform in a shape complimentary to the thread of the LAD. The deformed lugs create localized pressure points between the cap and LAD that provide additional securement and reduce the chance the cap and LAD will prematurely disengage. The lugs can be made of the same material as the thread and/or casing of the cap, or of a different material. Exemplary materials include the thermoplastic materials cited above. In some embodiments, where the LAD is made from polycarbonate blends having a Rockwell hardness of HRM 65-122 or HRR 72-123, the lugs are made from HDPE having a hardness of 55-75 Shore D (i.e. HRR 33-66) or low density polyethylene having a hardness of 38-56 Shore D. In a particular embodiment, the lugs are made from Alathon M5370 HDPE having a hardness of 67 Shore D.

Each of the lugs 34, 36 is located adjacent to the thread 30 but does not intersect the thread 30. The lugs may be located between the thread 30, as illustrated by first lug 34, and/or the lugs may be located below the thread, as illustrated by lug 36. The lugs can be located above the thread (not shown). However, this configuration is less favorable as the lug will make it slightly more difficult to align the threads of the LAD with the coupling mechanism to initiate engagement. The lugs 34, 36 can be offset from each other, as illustrated in FIG. 1, or the lugs can be arranged directly above and below each other.

Although lugs 34, 36 are rectangular in shape and extend in a vertical direction, as determined by an axis, y, extending from the bottom 22 to the top 20 of the casing 14, other shapes (e.g., z-shape, s-shape, squares, circles, ovals) and orientations are permissible. Generally, the shape and orientation of each lug should be such that when the thread of the LAD encounters a lug, the lug will plastically deform around the thread to create a localized pressure point which increases resistance between the thread of the LAD and the coupling mechanism. The increased resistance reduces the tendency of the LAD to prematurely disengage from the cap. In some embodiments, the dimension of the lug(s) in the vertical direction is at least 50%, at least 75%, or at least 90% of the distance between the thread (i.e., segments of thread directly above and below each other).

In some embodiments, the lugs provide increased resistance with increasing depth from the opening 16 of the casing 14. This is accomplished by increasing the volume (or mass) of lug material displaced by the LAD thread during engagement. The greater the volume of material displaced by the thread, the greater the localized pressure at that site. The maximum localized pressure should be large enough to reduce the incidence of unintended reverse threading but not so large that the user struggles to completely engage the cap. For example, in the embodiment illustrated in FIGS. 2-3, the first lug 34 has a height, $H_{L1}$, a length, $L_{L1}$, and a width, $W_{L1}$, and is located at a depth, $D_{L1}$, from the opening 16; the second lug 36 has a height, $H_{L2}$, a width, $W_{L2}$, and a length $L_{L2}$ and is located at a depth, $D_{L2}$, from the opening 16. As the depth of each lug increases (i.e. $D_{L1}<D_{L2}$), the volume, as approximated by the height, length and width of each lug, similarly increases (e.g., $H_{L1}<H_{L2}$; $L_{L1}<L_{L2}$; $W_{L1}<W_{L2}$ or $H_{L1}<H_{L2}$; $L_{L1}=L_{L2}$; $W_{L1}<W_{L2}$ or $H_{L1}<H_{L2}$; $L_{L1}=L_{L2}$; $W_{L1}=W_{L2}$). As used herein, the lug height, $H_L$, refers to the dimension of the lug that is perpendicular to the inner surface 24 of the casing 14, as illustrated in FIG. 3, and the lug width, $W_L$, and lug length $L_L$ are perpendicular to each other and the dimension $H_L$, as illustrated in FIGS. 2 and 3. The volume is approximate since the lugs may be slightly rounded due to, for example, drafting the lug to assist in demolding. However, the approximation accurately reflects the relative increase in volume between the first lug 34 and second lug 36. Generally, for any embodiment in the present application, the height of a lug, $H_L$, is no greater than the height of the thread, $H_T$, proximate thereto.

The increase in lug volume with corresponding increase in lug depth from the opening accommodates both short- and long-neck threaded devices. The short-neck devices encounter the lug(s) closest to the opening, providing additional resistance in the form of localized pressure points to minimize accidental disengagement. The long-neck devices will encounter additional lugs having localized pressure points with gradually increasing resistance as the LAD threads further into the interior cavity of the cap.

As the LAD threads onto the cap, it will be exposed to one or more cleaning agents. The cleaning agent can be a liquid, gel or solid depending upon the desired configuration. In some embodiments, the cleaning agent k a liquid that resides in the inner cavity. An optional seal or plunger may be used to hold the liquid cleaning agent in the bottom of the interior cavity. As the cap is threaded onto the LAD, the seal is ruptured or, alternatively, forced further into the interior cavity so that cleaning agent flows out around the seal, thus exposing the threads of the LAD to the cleaning agent. In other embodiments, a cleaning material (e.g., open cell foam or gauze) may contain the liquid cleaning agent. When the cap is threaded onto the LAD, the LAD comes in contact with the cleaning materials and the cleaning agent. In yet other embodiments, the cleaning agent is a gel that is coated on the inner surface of the casing and comes into contact with the LAD during the threading process. In yet other embodiments, the cleaning agent is integrated into the casing material as a solid.

Figure 4:
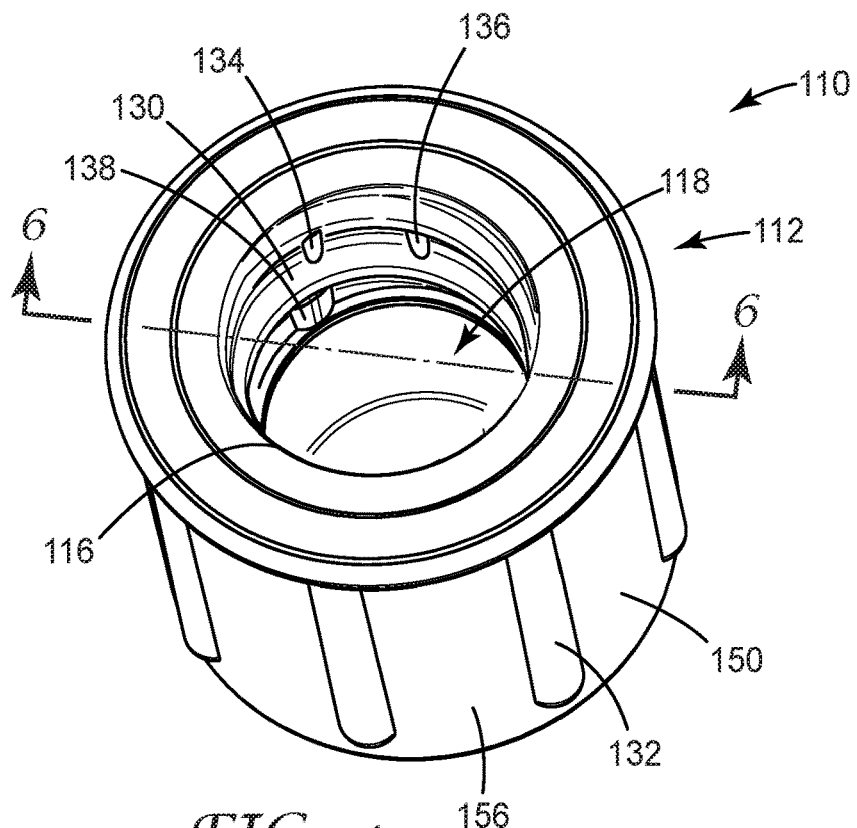
FIG. 4 is a top perspective view of a second exemplary cleaning device of the present application.
Figure 5:
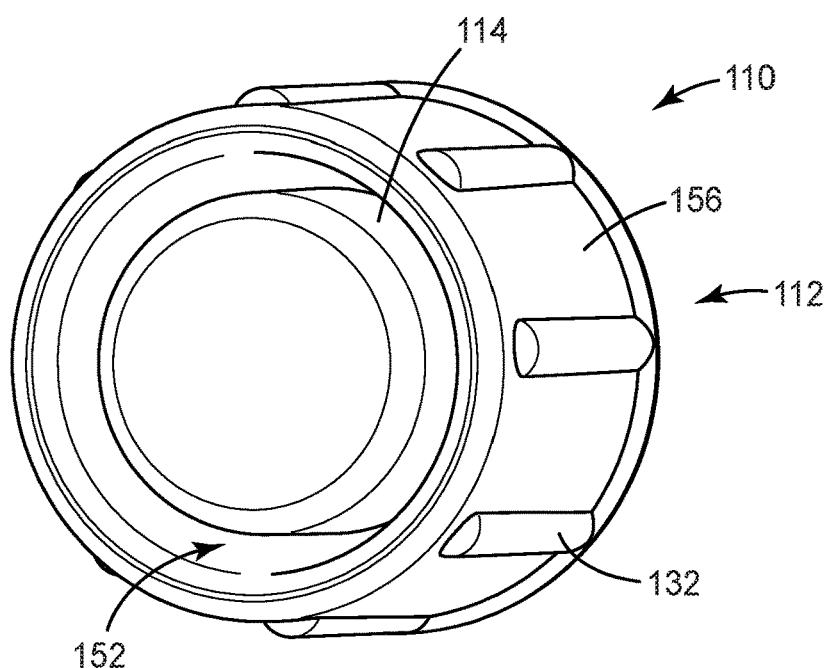
FIG. 5 is a bottom perspective view of the cleaning device shown in FIG. 4.
Figure 6:
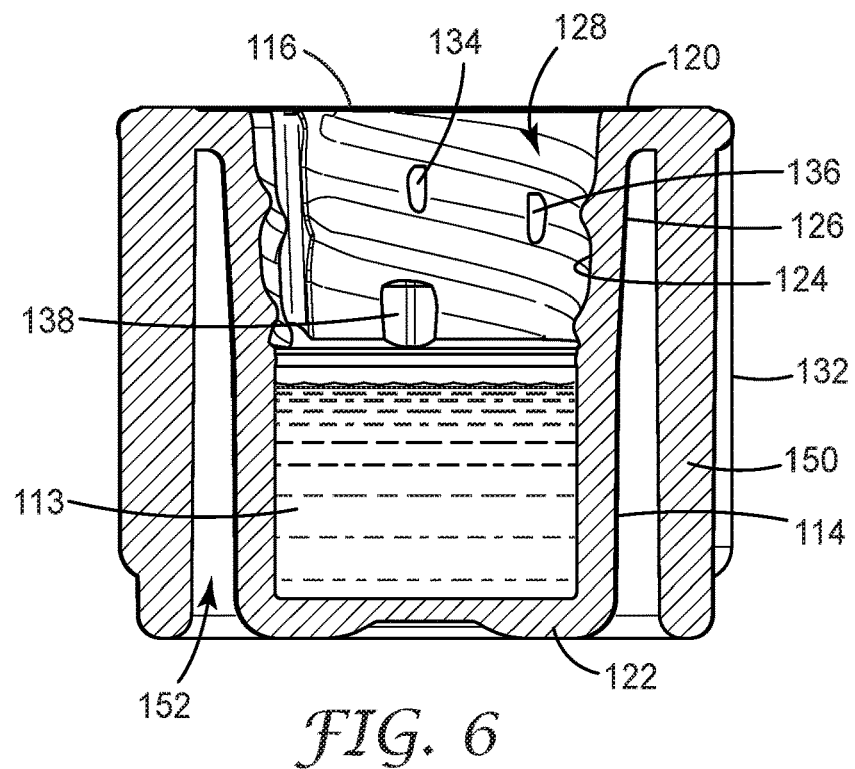
FIG. 6 is a cross-sectional view of the cleaning device shown in FIGS. 4 and 5 taken along line 6-6 in FIG. 4.

FIGS. 4-6 illustrate a second exemplary cleaning device 110 of the present application comprising a cap 112 and a cleaning agent 113. The cap 112 comprises a casing 114 having an opening 116 to an interior cavity 118. The casing 114 has a top 120, a bottom 122, an inner surface 124 and an outer surface 126. A coupling mechanism 128 is located on the inner surface 124 of the casing 114 proximate the opening 116. The coupling mechanism 128 is configured to engage with an externally threaded device, such as a LAD.

The cleaning device 110 shares many of the same elements and features described above with reference to the first exemplary embodiment illustrated in FIGS. 1-3. Accordingly, elements and features in the illustrated embodiment of FIGS. 4-6 are provided with the same reference numerals in the 100 series. Reference is made to the description above accompanying FIGS. 1-3 for a more complete description of the features and elements (and alternatives to such features and elements) of the cleaning device illustrated in FIGS. 4-6.

The second exemplary cleaning device differs from the first exemplary cleaning device in that a wall 150 circumscribes the outer surface 126 of the casing 114. The wall 150 is joined at the top 120 of the casing 114 and cantilevered over at least a portion of the outer surface 126 of the casing 114 to create an annular gap 152 between the wall 150 and the outer surface 126. The annular gap 152 allows for flexing or expansion of the casing 114 to accommodate variations in the diameter or width of the LADs. For example, a LAD may have an outer dimension that is wider than a specified width, which can be accommodated by bowing of the casing 114 due to the presence of the annular gap 152. The wall 150 may optionally have a number of gripping features 132 that are spaced around wall 150 on an external surface 156.

The coupling mechanism 128 of the second exemplary cleaning device also has a dual thread 130 and three lugs 134, 136, 138 instead of the two lugs in the first exemplary cleaning device. The first lug 134, second lug 136 and third lug 138 are located increasingly further into the interior cavity 118 and exhibit increasingly larger volumes of lug material.

The cleaning devices of the present application can be used on any LAD. In practice, the user removes the seal that covers the interior cavity of the disinfectant cap and threads the cap onto the LAD until securely engaged. During the engagement process, the thread of the LAD will meet increasing resistance as it passes through each lug. The resistance is large enough to enhance securement of the LAD and minimize premature disengagement, but is not so large that the cap is difficult to thread onto the LAD. LADs having a short neck, may encounter only one lug before becoming fully engaged. LADs having a longer neck, may encounter two or more lugs with progressively increased resistance.

Figure 7:
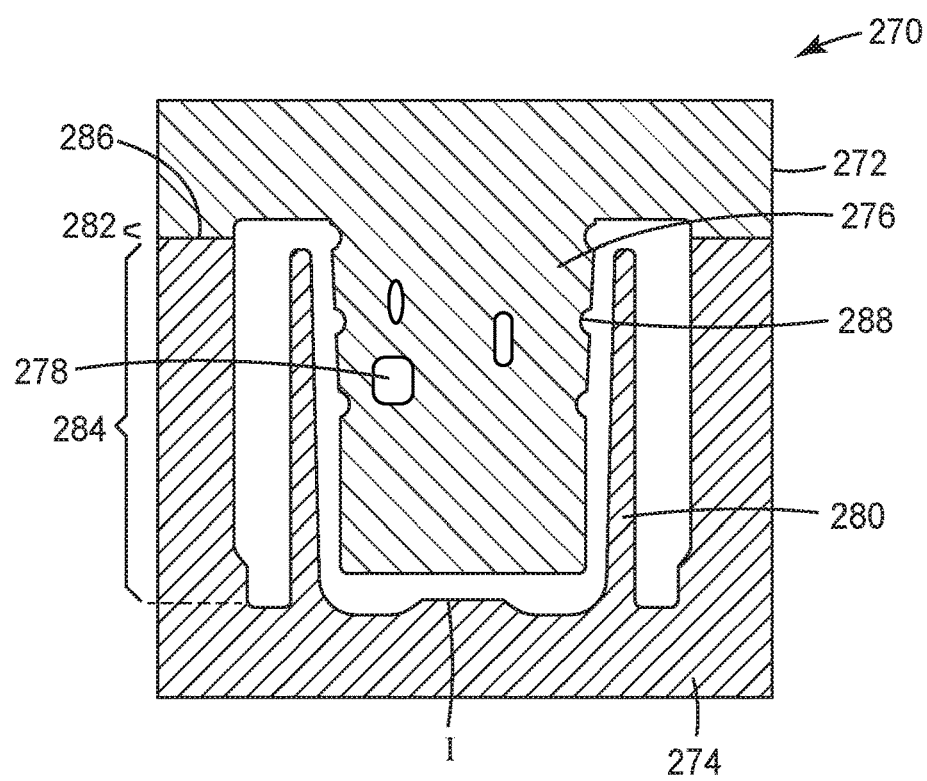
FIG. 7 is a cross-sectional view of an open and close mold that can be used to form a cleaning device of the present application.

FIG. 7 shows an open and close mold 270 that can be used to form a disinfectant cap 112 similar to that shown in FIGS. 4-6. The mold 270 includes a first side 272 and a second side 274. The first side 272 is shown to be separated from the second side 274 by the mold parting line 286. The first side 272 includes a mold core 276 that forms the interior cavity 118 shown in FIGS. 4-6. In particular, the mold core 276 includes a thread groove 288 and lug spaces 278 to form the thread 130 and lugs 134, 136, 138, respectively, of the cap. The second side 274 includes a feature 280 that forms the annular gap 152 shown in FIGS. 5 and 6.

The method involves injecting a liquid polymer into the mold 270 at a location 1. Injecting the polymeric material from the bottom of the mold 270 provides for a uniform material flow while filling the mold 270 and improves the moldability of the cap 112. The polymer is then allowed to cool so as to form the cap 112. After the polymeric material has solidified, the second side 274 is axially (without rotation) removed from the first side 272 of the mold 270. The cap is then axially (without rotation) removed from the first side 272 of the mold 270.

In some embodiments, the cap 112 is made of a resilient material which flexes during the demolding process and prevents the threading and lugs further in the interior of the cavity from deformation. As shown in FIG. 7, the mold comprises a constrained region 282 and an unconstrained region 284. Once the second side 274 of the mold 270 is removed, the casing 114 remains constrained in the first side 272 of the mold 270 but is unconstrained elsewhere. As the cap is removed from the first side 272 of the mold 270, the unconstrained region of the casing 114 flexes outward, preventing the mold from shaving down the thread and lugs that are further in the interior cavity.

One skilled in the art can easily adapt the mold in FIG. 7 to make the cap 12 illustrated in FIGS. 1-3 by eliminating the region in the mold used to create the wall 150.

The embodiments described above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention.

Thus, the present application discloses, among other things, a cleaning device and method of making such. Various features and advantages of the cleaning device are set forth in the following claims.

What is claimed is:

1. A cap comprising:
    a casing having an opening to an interior cavity, the casing having an inner surface and an outer surface; and
    a coupling mechanism on the inner surface of the casing proximate the opening, the coupling mechanism comprising:
        a thread that starts proximate the opening and spirals into the interior cavity;
        a first lug; and
        a second lug,
        wherein the first and second lugs do not intersect the thread and are between the thread, the first lug is closer to the opening of the casing than the second lug, and the volume of the second lug is greater than the volume of the first lug.

2. The cap of claim 1, further comprising a wall that circumscribes the outer surface of the casing, the wall joined at the top of the casing and cantilevered over at least a portion of the outer surface of the casing to create an annular gap between the wall and the outer surface.

3. The cap of claim 1, wherein the cap is made of a thermoplastic polymer.

4. The cap of claim 1, wherein the cap is made of high density polyethylene (HDPE).

5. The cap of claim 1, wherein the coupling mechanism comprises dual threads that do not intersect.

6. The cap of claim 1, wherein the height of the first lug is no greater than the height of the thread proximate thereto, and the height of the second lug is no greater than the height of the thread proximate thereto.

7. The cap of claim 1, wherein the width of the second lug is greater than the width of the first lug.

8. The cap of claim 1, further comprising one or more additional lugs.

9. The cap of claim 1, wherein the height of the thread increases with increasing distance from the opening.

10. A cleaning device comprising:
    a cap comprising an inner surface and an outer surface, with an opening to an inner cavity;
    a thread on the inner surface of the cap that starts proximate the opening and spirals into the inner cavity;
    a first lug; and
    a second lug;
    wherein the first and second lugs do not intersect the thread and are between to the thread; and wherein the first lug is closer to the opening than the second lug, and the volume of the second lug is greater than the volume of the first lug.

11. A cleaning device comprising:
a cap comprising
   a casing having an opening to an interior cavity, the casing having an inner surface and an outer surface;
   a coupling mechanism on the inner surface of the casing proximate the opening, the coupling mechanism comprising
     a thread that starts proximate the opening and spirals into the interior cavity;
     a first lug; and
     a second lug,
       wherein the first and second lugs do not intersect the thread and are between the thread, the first lug is closer to the opening of the casing than the second lug, and the volume of the second lug is greater than the volume of the first lug; and
a cleaning agent in the interior cavity of the casing.

12. The cleaning device of claim 11, wherein the cap further comprises a wall that circumscribes the outer surface of the casing, the wall joined at the top of the casing and cantilevered over at least a portion of the outer surface of the casing to create an annular gap between the wall and the outer surface.

13. The cleaning device of claim 12, wherein the casing is made of a resilient material that can flex into the annular gap when the cap is threaded onto an externally threaded device.

14. The cleaning device of claim 11, wherein the coupling mechanism is unitary with the casing.

15. The cleaning device of claim 11, wherein the cap is made of high density polyethylene (HDPE).

16. The cleaning device of claim 11, wherein the height of the first lug is no greater than the height of the thread proximate thereto, and the height of the second lug is no greater than the height of the thread proximate thereto.

17. The cleaning device of claim 11, wherein the width of the second lug is greater than the width of the first lug.

18. The cleaning device of claim 11, further comprising one or more additional lugs.

19. The cleaning device of claim 11, wherein the height of the thread increases with increasing distance from the opening.

20. The cleaning device of claim 11, wherein the cleaning agent is selected from the group consisting of alcohols, chlorhexidine, povidone-iodine, hydrogen peroxide, soap, hydrochloric acid, chloroxylenol (PMCX), polyhexamethylene biguanide (PHMB), octenidene, benzalkonium chloride, aqueous solutions thereof, and combinations thereof.

* * * * *

UNITED STATES PATENT AND TRADEMARK OFFICE
CERTIFICATE OF CORRECTION

| | | |
|---|---|---|
| PATENT NO. | : 10,617,780 B2 | Page 1 of 1 |
| APPLICATION NO. | : 15/623430 | |
| DATED | : April 14, 2020 | |
| INVENTOR(S) | : Alan Dombrowski | |

It is certified that error appears in the above-identified patent and that said Letters Patent is hereby corrected as shown below:

In the Specification

<u>Column 3</u>
Line 8                     Delete "(PMCX)," and insert -- (PCMX), --, therefor.
Line 9 (Approx.)           Delete "octenidene," and insert -- octenidine, --, therefor.

In the Claims

<u>Column 8</u>
Line 67                    In Claim 10, after "between" delete "to".

<u>Column 10</u>
Line 23                    In Claim 20, delete "(PMCX)," and insert -- (PCMX), --, therefor.
Line 24                    In Claim 20, delete "octenidene," and insert -- octenidine, --, therefor.

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*